United States Patent
Ikeda et al.

[11] Patent Number: 6,111,104
[45] Date of Patent: Aug. 29, 2000

[54] METHOD FOR REDUCING AN ORGANIC SOLVENT REMAINING IN TRIS-(2,3-EPOXYPROPYL)-ISOCYANURATE CRYSTALS

[75] Inventors: Hisao Ikeda; Yasuhiro Gunji; Toshinari Koda; Motohiko Hidaka, all of Chiba; Atsumi Aoki, Yamaguchi, all of Japan

[73] Assignee: Nissan Chemical Industries, Ltd., Tokyo, Japan

[21] Appl. No.: 09/362,710

[22] Filed: Jul. 29, 1999

[30] Foreign Application Priority Data

Sep. 1, 1998 [JP] Japan ................... 10-246758

[51] Int. Cl.⁷ ................................ C07D 251/30
[52] U.S. Cl. .................................. 544/221
[58] Field of Search ............................. 544/221

[56] References Cited

U.S. PATENT DOCUMENTS

| | | | |
|---|---|---|---|
| 3,300,490 | 1/1967 | Budnowski | 544/221 |
| 3,337,509 | 8/1967 | Budnowski | 544/221 |
| 3,547,918 | 12/1970 | Porret et al. | 544/221 |
| 4,988,395 | 1/1991 | Taguchi et al. | |
| 5,116,945 | 5/1992 | Osawa et al. | |
| 5,719,281 | 2/1998 | Gutschoven et al. | 544/221 |
| 5,892,065 | 4/1999 | Tsukamoto et al. | |

FOREIGN PATENT DOCUMENTS

| | | |
|---|---|---|
| 0 822 189 | 2/1998 | European Pat. Off. . |
| 96/26900 | 9/1996 | WIPO . |

OTHER PUBLICATIONS

Derwent Publications, AN 1991–129136, JP 03 068568, Mar. 25, 1991.

Derwent Publications, AN 1994–163919, JP 06 107659, Apr. 19, 1994.

*Primary Examiner*—Richard L. Raymond
*Assistant Examiner*—Venkataraman Balasubramanian
*Attorney, Agent, or Firm*—Oblon, Spivak, McClelland, Maier & Neustadt, P.C.

[57] ABSTRACT

A method for reducing an organic solvent remaining in tris-(2,3-epoxypropyl)-isocyanurate crystals, which comprises pulverizing crystal particles of tris-(2,3-epoxypropyl)-isocyanurate while evaporating a volatile component from the surface of the particles.

11 Claims, No Drawings

METHOD FOR REDUCING AN ORGANIC SOLVENT REMAINING IN TRIS-(2,3-EPOXYPROPYL)-ISOCYANURATE CRYSTALS

The present invention relates to a method for reducing an organic solvent remaining in tris-(2,3-epoxypropyl)-isocyanurate crystals, by removing the organic solvent remaining in said crystals while evaporating a volatile component from the surface of the crystals, particularly by e.g. machine pulverization in a gas stream.

In view of an increasing demand in recent years for the properties required for a solder resist material, such as adhesion, electrical insulating properties, soldering heat resistance and solvent resistance, a solder resist ink composition is presently used which is a combination of a photosensitive prepolymer and a thermosetting resin. Namely, it is designed to satisfy the above required properties by forming a solder resist pattern by the photosensitive prepolymer, followed by thermosetting. Further, demands have been increasing for high densification of printed circuit boards along with a trend for light weight and miniaturization of electronic appliances in recent years, for low bleeding during formation of solder resist patterns for surface mounting of parts and for precision in embedding between circuits. Accordingly, as the thermosetting resin to be incorporated to the solder resist ink, a fine particulate solid epoxy having high solvent resistance is desired.

As a solid epoxy to satisfy the above required properties, tris-(2,3-epoxypropyl)-isocyanurate may be mentioned. Tris-(2,3-epoxypropyl)-isocyanurate has three asymmetric carbon atoms, and crystals made of an equimolar mixture of (2R,2'R,2"R)-tris-(2,3-epoxypropyl)-isocyanurate and (2S,2'S,2"S)-tris-(2,3-epoxypropyl)-isocyanurate, wherein all of the three asymmetric carbon atoms are optically isotropic, are commonly called β-form crystals and known to give crystals having a high melting point of a level of about 150° C. This is attributable to the fact that a pair of these two types of enantiomers form a molecular lattice having six firm hydrogen bonds and thus form a crystal lattice. On the other hand, crystals made of a mixture of (2R,2R,2S)-tris-(2,3-epoxypropyl)-isocyanurate and (2S,2S,2R)-tris-(2,3-epoxypropyl)-isocyanurate, wherein one of the three asymmetric carbon atoms is different in the optical anisotropy, are commonly called α-form crystals, and they do not have the above crystal structure and accordingly present only a low melting point of a level of about 100° C. The β-form tris-(2,3-epoxypropyl)-isocyanurate crystals not only have a high melting point but also have a low solubility in various solvents. Accordingly, when they are used as a crosslinking agent for different types of compounds or for reactive polymers in the form of a one pack type reactive mixture, the reaction will not proceed during storage, until they are forcibly cured. Such β-form crystals have been used for applications to electric and electronic materials, for example, as a solder resist ink composition of photocuring/thermosetting combined type.

The liquid epoxy composition is likely to undergo an increase in viscosity during storage, since a part of the epoxy compound dissolves in the solvent, and entanglement with the photosensitive prepolymer is likely to result, whereby elution tends to be poor during washing off of the non-exposed portion. JP-B-7-17737 discloses use of β-form tris-(2,3-epoxypropyl)-isocyanurate as a hardly soluble epoxy compound. β-form tris-(2,3-epoxypropyl)-isocyanurate fine particles which have a high melting point and which are hardly soluble, are in a state enclosed by a photosensitive prepolymer, whereby they will not reduce the solubility of the photosensitive prepolymer at the non-exposed portion. Further, they are hardly soluble in an organic solvent, whereby the exposed portion is hardly eroded by a developer, whereby there will be no deterioration in the sensitivity. Further, the storage stability of the solder resist ink composition is excellent.

As a method for separating β-form tris-(2,3-epoxypropyl)-isocyanurate and α-form tris-(2,3-epoxypropyl)-isocyanurate from tris-(2,3-epoxypropyl)-isocyanurate, a separation method has been available wherein a solvent which dissolves α-form tris-(2,3-epoxypropyl)-isocyanurate relatively well and which hardly dissolves β-form tris-(2,3-epoxypropyl)-isocyanurate, for example, an alcohol such as methanol, is employed. For example, Journal of Thermal Analysis, vol.36 (1990) p.1819 discloses separation by means of a methanol solvent. Further, Plaste und Kautschuk 23 Jahrgang Heft 4/1975 discloses a method wherein firstly a methanol solvent is used for separating β-form tris-(2,3-epoxypropyl)-isocyanurate, and then the β-form tris-(2,3-epoxypropyl)-isocyanurate is purified by chloroform. Further, Kobunshi Ronbunshu (polymer report collection), vol.47, No.3 (1990) p.169, discloses a method wherein synthesized tris-(2,3-epoxypropyl)-isocyanurate is put into methanol, followed by heating and stirring, whereupon the non-dissolved content is collected by filtration, and the obtained non-dissolved substance is re-crystallized from methyl ethyl ketone to obtain β-form tris-(2,3-epoxypropyl)-isocyanurate crystals.

Many of β-form tris-(2,3-epoxypropyl)-isocyanurates obtained by such separation methods, hardly undergo crystal growth, and many of them have a small particle size, whereby the filtration operation in the filtration step tends to be very difficult. Accordingly, it is undesirable that the crystals obtained by crystallization are too fine.

Further, by a single separation operation by the foregoing separation method, β-form tris-(2,3-epoxypropyl)-isocyanurate crystals tend to contain the solvent for crystallization, chlorine-containing impurities or other impurities. Accordingly, it will be necessary to remove them by further carrying out recrystallization or by melting the crystals once.

JP-B-48-24039 discloses a process wherein a chlorohydrin ester of isocyanuric acid obtained by reacting cyanuric acid with epichlorohydrin, is dehydrochlorinated with an alkali, and the alkali metal chloride thereby formed, is separated, and the obtained epichlorohydrin solution of tris-(2,3-epoxypropyl)-isocyanurate, is concentrated to a tris-(2,3-epoxypropyl)-isocyanurate concentration of from 50 to 60%, and then the solution is cooled to from 20 to 25° C. to obtain tris-(2,3-epoxypropyl)-isocyanurate crystals in an yield of 27% based on cyanuric acid. However, the crystals are obtained by crystallization from the epichlorohydrin solution, whereby a large amount of epichlorohydrin, etc. are contained in the interior of the crystals. Further, epichlorohydrin is composed of a hydrolyzable chlorine which is not only hazardous to human bodies but also hazardous to applications to electronic materials, and should be contained as little as possible. Epichlorohydrin remaining in the crystals can be removed only by heating the crystals to at least the melting point to melt the crystals. Such a method makes the production step more complicated, and costs much, whereby it is not practical industrially.

The present invention provides a method to make the amount of an organic solvent, particularly epichlorohydrin, remaining in tris-(2,3-epoxypropyl)-isocyanurate crystals, particularly β-form tris-(2,3-epoxypropyl)-isocyanurate crystals, extremely small.

The present invention resides in a method for reducing an organic solvent remaining in tris-(2,3-epoxypropyl)-isocyanurate crystals, which comprises pulverizing crystal particles of tris-(2,3-epoxypropyl)-isocyanurate while evaporating a volatile component from the surface of the particles.

Now, the present invention will be described in detail with reference to the preferred embodiments.

In the present invention, as the pulverization while evaporating a volatile component from the surface of the particles, a pulverization carried out in a gas stream, or a pulverization carried out under reduced pressure, may be mentioned. The pulverization carried out in a gas stream is particularly effective.

The pulverization in a gas stream is carried out by using a pulverizer such as 200 AFG Model counter jet mill manufactured by ALPINE or KJ-200 Model cross jet mill manufactured by Kurimoto Ltd. The mechanism of such types of pulverizers is such that a high pressure air or inert gas such as nitrogen is sprayed into the pulverizer together with a sample, and the sample particles collide with one another and are pulverized. The pressure of the gas is from 1 to 10 kg/cm$^2$. By the gas stream, a volatile component evaporates from the surface of particles which are newly formed by the pulverization, and an organic solvent contained in the crystals is reduced. The crystal particles are pulverized to an average particle size of from 0.5 to 20 $\mu$m. At this time, the concentration of the organic solvent remaining in the pulverized crystal particles is at most 300 ppm, usually from 100 to 200 ppm.

The crystal particles of tris-(2,3-epoxypropyl)-isocyanurate of the present invention may be any crystals of tris-(2,3-epoxypropyl)-isocyanurate having an average particle size of from 20 to 500 $\mu$m. However, crystal particles of β-form tris-(2,3-epoxypropyl)-isocyanurate are particularly preferred. The β-form tris-(2,3-epoxypropyl)-isocyanurate crystals are obtained, for example, by reacting cyanuric acid with epichlorohydrin in the presence of a catalyst to form a chlorohydrin ester of isocyanuric acid, followed by dehydrochlorination with an alkali, separating off the resulting alkali metal salt to obtain a reaction solution containing tris-(2,3-epoxypropyl)-isocyanurate, and crystallizing it out of the solution.

In the above-mentioned method for carrying out the crystallization from the reaction solution, the remaining organic solvent is epichlorohydrin.

The above-mentioned process for producing β-form tris-(2,3-epoxypropyl)-isocyanurate crystals from the reaction solution comprises the following steps (A), (B), (C), (D) and (E):

(A) a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a tri-substituted phosphine and a quaternary phosphonium salt, as a catalyst, to obtain a reaction solution, adding from 3 to 6 mols of an alkali metal hydroxide or an alkali metal alcoholate to the reaction solution for dehydrochlorination, and removing the resulting alkali metal salt to obtain a reaction solution containing tris-(2,3-epoxypropyl)-isocyanurate, (B) a step of adjusting the reaction solution containing tris-(2,3-epoxypropyl)-isocyanurate obtained in step (A) to a solid content concentration of from 10 to 50 wt %, (C) a step of adding seed crystals to the liquid obtained in step (B) at a temperature lower by from 5 to 20° C. than the temperature at which the liquid forms a saturated solution, (D) a step of gradually cooling the liquid obtained in step (C) at a cooling rate of not higher than 20° C./hr for crystallization, followed by filtration to obtain crystals, and (E) a step of washing the crystals obtained in step (D)

In step (A) in the process for producing β-form tris-(2,3-epoxypropyl)-isocyanurate crystals, (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a tri-substituted phosphine and a quaternary phosphonium salt, as a catalyst, are reacted.

As examples of the catalyst (c), the tertiary amine may, for example, be tripropylamine, tributylamine or N,N'-dimethylpiperazine. The quaternary ammonium salt may, for example, be tetramethylammonium halide, tetraethylammonium halide or tetrabutylammonium halide, wherein the halide may, for example, be chloride, bromide or iodide. The quaternary ammonium base may, for example, be tetramethylammonium hydroxide or benzyltrimethylammonium hydroxide. The tri-substituted phosphine may, for example, be tripropylphosphine, tributylphosphine, triphenylphosphine or tritolylphosphine, and the quaternary phosphonium salt may, for example, be tetramethylphosphonium halide, tetrabutylphosphonium halide, methyltriphenylphosphonium halide or ethyltriphenylphosphonium halide, wherein the halide may, for example, be chloride, bromide or iodide. Among the above-mentioned compounds, a quaternary ammonium salt or a quaternary phosphonium salt is particularly preferred since the reaction proceeds efficiently under a mild condition with no substantial side reaction. Particularly preferred is a quaternary ammonium salt, such as tetramethylammonium halide, tetraethylammonium halide or tetrabutylammonium halide, wherein the halide is chloride or bromide, whereby the side reactions can further be suppressed, and removal of the catalyst after the reaction can easily be made simply by washing with water.

To the reaction solution thus obtained, from 3 to 6 mols of an alkali metal hydroxide or an alkali metal alcoholate is added for dehydrochlorination, and the resulting alkali metal salt is separate off by washing with water or filtration, to obtain a reaction solution containing tris-(2,3-epoxypropyl)-isocyanurate. As such an alkali metal hydroxide, sodium hydroxide, potassium hydroxide or lithium hydroxide may, for example, be mentioned, and as such an alkali metal alcoholate, sodium methylate, sodium ethylate, potassium methylate or potassium ethylate may, for example, be mentioned. The tris-(2,3-epoxypropyl)-isocyanurate thus obtained, contains β-form tris-(2,3-epoxypropyl)-isocyanurate and α-form tris-(2,3-epoxypropyl)-isocyanurate in a weight ratio of 1:3.

The reaction solution containing tris-(2,3-epoxypropyl)-isocyanurate thus obtained, is then adjusted by concentration or dilution to a concentration suitable for crystallization. For the measurement of the solid content concentration, the reaction solution is treated by a rotary evaporator at 120° C. under a pressure of not higher than 5 Torr for 3 hours for evaporation to dryness, whereupon the solid content weight is measured, and the solid content concentration can be calculated.

In step (B), the solid content concentration of the reaction solution containing tris-(2,3-epoxypropyl)-isocyanurate is adjusted to a level of from 10 wt % to 50 wt %, preferably from 25 wt % to 40 wt %.

If this concentration is too low, the cooling temperature required for crystallization must be lowered to a low level, and no adequate yield can be attained.

On the other hand, if this concentration is too high, the cooling temperature required for crystallization must be maintained at a high temperature.

Consequently, the filtration temperature must be maintained at a high temperature.

The necessity for maintaining the cooling temperature range required for this crystallization is to let the β-form, rather than the α-form, be selectively contained in the precipitated crystals.

Table 1 shows the relation between the solid content concentration (%) of tris-(2,3-epoxypropyl)-isocyanurate in the reaction solution, and the temperature (° C.) for forming a saturated solution and the cooling temperature (° C.) required for crystallization. Here, the temperature for forming a saturated solution is determined in such a manner that the reaction solution obtained in step (B) is evaporated to dryness at 120° C. under 2 Torr to obtain tris-(2,3-epoxypropyl)-isocyanurate, which is pulverized to obtain a powder of at most 32 mesh, which is adjusted to a predetermined solid content concentration with epichlorohydrin, followed by heating at a temperature-raising rate of 1° C./min from room temperature with vigorous stirring, whereby the temperature when the solid has dissolved completely, is taken as the temperature for forming a saturated solution.

TABLE 1

| Solid content concentration (%) of tris-(2,3-epoxypropyl)-isocyanurate | 50 | 40 | 30 | 25 | 15 | 10 |
|---|---|---|---|---|---|---|
| Temperature (° C.) for forming a saturated solution | 79 | 69 | 58 | 53 | 39 | 29 |
| Cooling temperature (° C.) required for crystallization | 35 ± 5 | 25 ± 5 | 15 ± 5 | 11 ± 5 | 0 ± 5 | −5 ± 5 |

In step (C), seed crystals are added to the liquid obtained in step (B) at a temperature lower by from 5 to 20° C. than the temperature at which this liquid forms a saturated solution.

As seed crystals, β-form or α-form tris-(2,3-epoxypropyl)-isocyanurate is used. If crystallization is carried out without adding seed crystals, a supersaturated state will continue even during cooling, and at a later half of cooling, crystallization takes place all at once. This is not desirable since the purity deteriorates due to inclusion of impurities such as epichlorohydrin and α-form tris-(2,3-epoxypropyl)-isocyanurate.

In step (C), prior to the addition of seed crystals, the reaction solution may be heated to a temperature of at least the temperature for forming a saturated solution to adequately dissolve tris-(2,3-epoxypropyl)-isocyanurate in the reaction solution, and then it is gradually cooled to a temperature lower by from 5 to 20° C. than the temperature for forming a saturated solution, and then seed crystals may be added. By this method, the average particle size of the obtained crystals will be uniform, such being desirable in view of the filtration properties, etc.

In the present invention, crystal growth starts from the added seed crystals as nuclei.

If step (C) is carried out without heating the reaction solution to a temperature of at least the temperature for forming a saturated solution, while maintaining it at a temperature lower by from 5 to 20° C. than the temperature for forming a saturated solution, fine crystals will be formed in the reaction solution at this temperature, and such crystals will also serve as seed crystals together with the subsequently added seed crystals, whereby it tends to be difficult to control the number of seed crystals. Accordingly, it is preferred that the reaction solution is heated once to a temperature of at least the temperature for forming a saturated solution, then it is cooled to a temperature lower by from 5 to 20° C. than the temperature for forming a saturated solution, and then seed crystals are added.

After adding the seed crystals in step (C), it is preferred to carry out stirring at the temperature for the addition for from 0.5 to 1 hour.

In the subsequent step (D), the liquid is gradually cooled. This cooling rate is at most 20° C./hr, preferably at most 10° C./hr. If the cooling is carried out rapidly, rapid crystal precipitation will take place, and the purity will decrease due to inclusion of impurities, such being undesirable.

In the process for producing β-form tris-(2,3-epoxypropyl)-isocyanurate crystals, seed crystals may not be added in step (C). In such a case, it is necessary to carry out crystallization gradually over a long period of time in step (D). In such a case, it is necessary to gradually cool the liquid with the cooling rate of e.g. at most 5° C./hr.

The precipitated β-form tris-(2,3-epoxypropyl)-isocyanurate crystals will be separated by filtration such as suction filtration, filter press filtration or centrifugal filtration.

In step (E), the β-form tris-(2,3-epoxypropyl)-isocyanurate obtained by filtration, can be washed with various organic solvents, since it contains impurities, or α-form tris-(2,3-epoxypropyl)-isocyanurate and epichlorohydrin. The organic solvents include, for example, methanol, ethanol, isopropyl alcohol, methyl ethyl ketone, acetonitrile, dimethylformamide, and epichlorohydrin.

The washing can be carried out at a temperature of from 5 to 50° C., preferably from 5 to 30° C. At a high temperature such as from 30 to 50° C., the solubility increases, and the amount of the solvent can be saved, but the operation will be at a temperature close to the boiling point or the flash point. A centrifugal filtration machine has a possible danger of inflammation due to static electricity, and a highly safe pressure filtration machine has a possible problem such that α-form tris-(2,3-epoxypropyl)-isocyanurate dissolved in the washing solvent is likely to recrystallize in the filter material or in the cake by the passage of pressurizing gas, whereby the filtration property tends to deteriorate. Further, there will be a restriction such that a preheating installation for the solvent and a temperature-keeping installation not to let α-form tris-(2,3-epoxypropyl)-isocyanurate reprecipitate from the recovered solvent, will be required. Further, at a temperature of 50° C. or higher, a special thermal filtration system will be required. On the other hand, at a temperature lower than 5° C., a large amount of the solvent will be required.

The β-form tris-(2,3-epoxypropyl)-isocyanurate crystals obtained through step (E), have an average particle size of from 10 to 500 μm. In the present invention, crystals having an average particle size of exceeding 20 μm and at most 500 μm may be used.

By drying the β-form tris-(2,3-epoxypropyl)-isocyanurate crystals obtained in step (E) at a temperature of from 100 to 140° C., preferably from 120 to 140° C., in a gas stream under normal pressure or under reduced pressure, the remaining epichlorohydrin may be reduced to at most 1,000 ppm, particularly preferably at most 300 ppm. The above temperature of from 100 to 140° C., preferably from 120 to 140° C., is a temperature of at least the melting point of α-form tris-(2,3-epoxypropyl)-isocyanurate and a temperature of at most the melting point of β-form tris-(2,3-epoxypropyl)-isocyanurate. When the drying is carried out at this temperature in a gas stream, in the β-form tris-(2,3-epoxypropyl)-isocyanurate crystals containing α-form tris-(2,3-epoxypropyl)-isocyanurate in the interior of the crystals, a part of the α-form tris-(2,3-epoxypropyl)-isocyanurate will be melted and liquefied. Through this liquid portion, epichlorohydrin as an impurity will be discharged from the crystals out of the crystals.

However, in the present invention, the organic solvent remaining in the β-form tris-(2,3-epoxypropyl)-isocyanurate crystals obtained in step (E) can be reduced only by carrying out a step of pulverizing the crystals in a gas stream, without a step of drying at a temperature of from 100 to 140° C., preferably from 120 to 140° C.

The pulverization is carried out by pulverizing the β-form tris-(2,3-epoxypropyl)-isocyanurate crystals to an average particle size of from 0.5 to 20 μm. By the pulverization, the remaining organic solvent can be reduced to at most 300 ppm.

The average particle size and the particle size distribution of the pulverized product can be controlled by pulverization conditions or a classifying rotor. When the β-form tris-(2,3-epoxypropyl)-isocyanurate crystals are pulverized to an average particle size of from 0.5 to 20 μm, the organic solvent in the interior of the crystals can effectively be removed. The smaller the average particle size of the pulverized crystals, the higher the removal ratio of the solvent. However, if the average particle size is smaller than this range, the pulverization efficiency tends to be low. Further, if the average particle size is at least 20 μm, the removal ratio of the solvent tends to be low.

Method for Quantitative Analysis of Epichlorohydrin Remaining in the Crystals

Epichlorohydrin remaining in the crystals is determined in such a manner that to the sample (the crystals), 20 times of dimethylformamide is added and dissolved by heating to 80° C., followed by quantitative analysis by gas chromatography.

Now, the present invention will be described in further detail with reference to Examples. However, it should be understood that the present invention is by no means restricted to such specific Examples.

Production Example for β-form Tris-(2,3-epoxypropyl)-Isocyanurate Crystals

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): A part of epichlorohydrin was distilled off under reduced pressure at a temperature of 70° C. until the solid content concentration in the reaction solution became 40 wt %, to obtain 4,000 g of an adjusted liquid.

Step (C): The temperature was cooled to 60° C., whereupon 11.2 g of β-form tris-(2,3-epoxypropyl)-isocyanurate was added as seed crystals.

Step (D): The liquid was cooled to 25° C. over 4 hours to precipitate β-form tris-(2,3-epoxypropyl)-isocyanurate crystals, which were collected by filtration.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 700 ppm, an epoxy equivalent of 101 g/eq., a melting point of from 148 to 158° C., and an average particle size of 75 μm, and they were white crystals.

EXAMPLE 1

The β-form tris-(2,3-epoxypropyl)-isocyanurate crystals obtained in Production Example were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals having an average particle size of 75 μm were pulverized to fine particles having an average particle size of 3.0 μm, and the remaining epichlorohydrin was reduced from 700 ppm to 180 ppm.

EXAMPLE 2

The β-form tris-(2,3-epoxypropyl)-isocyanurate crystals obtained in Production Example were pulverized by 200 AFG Model counter jet mill manufactured by ALPINE. The pulverization was carried out under a nitrogen pressure of 6.0 kg/cm$^2$, with a nitrogen amount of 800 Nm3/h, with a sample-supplying rate of 30 kg/h, and with a classifying rotor rotated at 12,000 rpm. By the pulverization, the crystals having an average particle size of 75 μm were pulverized to fine particles having an average particle size of 1.5 μm, and the remaining epichlorohydrin was reduced to 90 ppm.

REFERENCE EXAMPLE 1

The crystals obtained in Production Example were further dried at 120° C. under a reduced pressure of 5 Torr for 4 hours. The remaining epichlorohydrin was 200 ppm.

By the present invention, an organic solvent remaining in tris-(2,3-epoxypropyl)-isocyanurate crystals can be removed by pulverizing crystal particles of tris-(2,3-epoxypropyl)-isocyanurate to an average particle size of from 0.5 to 20 μm, while evaporating a volatile component from the surface of the particles.

With tris-(2,3-epoxypropyl)-isocyanurate crystals obtained by a conventional recrystallization method, the remaining organic solvent involved in the interior of the crystals has been removed by heating to a temperature of at least the melting point of tris-(2,3-epoxypropyl)-isocyanurate. For β-form tris-(2,3-epoxypropyl)-isocyanurate crystals, heating at a temperature of at least 150° C. has been necessary.

Further, in a method for precipitating β-form tris-(2,3-epoxypropyl)-isocyanurate crystals containing α-form tris- (2,3-epoxypropyl)-isocyanurate from a reaction solution containing tris-(2,3-epoxypropyl)-isocyanurate, the organic solvent (epichlorohydrin) may be removed in such a manner that the crystals are heated to a temperature of from 100 to 140° C., preferably from 120 to 140° C., to melt α-form tris-(2,3-epoxypropyl)-isocyanurate in said crystals, and through this melted portion in the crystals, the organic solvent may be removed. However, in the present invention, the organic solvent can be removed only by pulverizing the tris-(2,3-epoxypropyl)-isocyanurate crystals in a gas stream. The present invention is particularly effective for removing the organic solvent remaining in the β-form tris-(2,3-epoxypropyl)-isocyanurate crystals.

What is claimed is:

1. A method of evaporatively treating tris-(2,3-epoxypropyl)-isocyanurate crystals, comprising:

pulverizing crystal particles of tris-(2,3-epoxypropyl)-isocyanurate, which have been washed with an organic solvent which effectively removes impurities from the crystals which are present therein as a result of the preparation of tris-(2,3-epoxypropyl)-isocyanurate, while evaporating said solvent and epichlorohydrin reactant from the surfaces of the particles.

2. The method of claim 1, wherein the pulverization with evaporation occurs in a pulverizing device under a stream of air or an inert gas passing through the pulverizer at a pressure of 1–10 kg/cm$^2$, said pulverization reducing the average particle size of the crystals to 0.5–20 μm.

3. The method of claim 1, wherein evaporation occurs at a temperature of 100–140° C.

4. The method of claim 3, wherein said temperature ranges from 120–140° C.

5. The method of claim 2, wherein the particles of tris-(2,3-epoxypropyl)-isocyanurate placed in said pulverizing apparatus range in average particle size from greater than 20–500 μm.

6. The method of claim 1, wherein the concentration of organic solvent remaining in the pulverized particles is at most 300 ppm.

7. The method of claim 1, wherein the crystal particles of tris-(2,3-epoxypropyl)-isocyanurate are in the β-form.

8. The method of claim 7, wherein the crystals of tris-(2,3-epoxypropyl)-isocyanurate in β-form are prepared by reacting cyanuric acid with epichlorohydrin in the presence of a catalyst, thereby forming a chlorohydrin ester of isocyanuric acid, followed by dehydrochlorinating the chlorohydrin ester with an alkali, separating the resulting alkali metal salt thereby resulting in a reaction solution containing tris-(2,3-epoxpropyl)-isocyanurate, and then crystallizing the tris-(2,3-epoxpropyl)-isocyanurate from solution.

9. The method of claim 6, wherein the remaining organic solvent is epichlorohydrin.

10. The method of claim 1, wherein the organic solvent employed for washing of crystals of tris-(2,3-epoxypropyl)-isocyanurate is selected from the group consisting of methanol, ethanol, isopropyl alcohol, methyl ethyl ketone, acetonitrile, dimethylformamide and epichlorohydrin.

11. The method of claim 2, wherein said inert gas is nitrogen.

* * * * *